(12) United States Patent
Neeser et al.

(10) Patent No.: US 7,767,430 B2
(45) Date of Patent: Aug. 3, 2010

(54) BIFIDOBACTERIA PREVENTING DIARRHEA CAUSED BY PATHOGENIC BACTERIA

(75) Inventors: Jean-Richard Neeser, Savigny (CH); Roberto Reniero, Le Mont-Pelerin (CH); Florence Rochat, Montreux (CH); Alain Servin, Chatenay-Malabry (FR)

(73) Assignee: Nestec S.A., Vevey (CH)

( * ) Notice: Subject to any disclaimer, the term of this patent is extended or adjusted under 35 U.S.C. 154(b) by 323 days.

(21) Appl. No.: 11/171,014

(22) Filed: Jun. 30, 2005

(65) Prior Publication Data

US 2005/0260170 A1 Nov. 24, 2005

Related U.S. Application Data

(62) Division of application No. 10/048,657, filed as application No. PCT/EP00/07208 on Jul. 26, 2000, now Pat. No. 6,926,891.

(30) Foreign Application Priority Data

Aug. 5, 1999 (EP) .................................. 99115502

(51) Int. Cl.
*C12N 1/20* (2006.01)

(52) U.S. Cl. ................ 435/252.1; 424/93.4; 435/252.9; 426/61

(58) Field of Classification Search ....................... None
See application file for complete search history.

(56) References Cited

U.S. PATENT DOCUMENTS

| 5,494,664 | A | 2/1996 | Brassart et al. |
| 6,077,504 | A | 6/2000 | Cavaliere ved. Vesley et al. |

FOREIGN PATENT DOCUMENTS

| EP | 0 577 903 | | 1/1994 |
| EP | 0 768 375 | A1 | 4/1997 |
| WO | WO 97/00078 | | 1/1997 |

OTHER PUBLICATIONS

Martin et al., Cultured Dairy Products Journal, Nov. 1992, pp. 21-26.*
XP-000857900, Adhesion of Human Bifidobacterial Strains to Cultured Human Intestinal Epithelial Cells and Inhibition of Enteropathogen-Cell Interactions, Bernet et al, vol. 59, pp. 4121-4128.

* cited by examiner

*Primary Examiner*—Irene Marx
(74) *Attorney, Agent, or Firm*—K&L Gates LLP

(57) ABSTRACT

The present invention pertains to novel microorganisms of the genus *Bifidobacterium*, that are useful in preventing diarrhea brought about by pathogenic bacteria. In particular, the present invention relates to the use of said microorganisms for the preparation of an ingestable support and to a composition containing the same.

3 Claims, 5 Drawing Sheets

BIFIDOBACTERIA PREVENTING DIARRHEA CAUSED BY PATHOGENIC BACTERIA

CROSS REFERENCE TO RELATED APPLICATIONS

This patent application is a divisional of U.S. application Ser. No. 10/048,657 filed on Apr. 22, 2002, now U.S. Pat. No. 6,926,891 which was the National Stage of International Application No. PCT/EP00/07208, filed on Jul. 26, 2000 the disclosures of which are herein incorporated by reference.

BACKGROUND

The present invention pertains to novel microorganisms of the genus *Bifidobacterium*, that are useful in preventing diarrhea brought about by pathogenic bacteria. In particular, the present invention relates to the use of said microorganisms for the preparation of an ingestable support and to a composition containing the same.

Organisms that produce lactic acid as a major metabolic component have been known since long. These bacteria may be found in milk or in milk processing factories, respectively living or decaying plants but also in the intestine of man and animals. These microorganisms, summarized under the term "lactic acid bacteria", represent a rather inhomogeneous group and comprise e.g. the genera *Lactococcus, Lactobacillus, Streptococcus, Bifidobacterium, Pediococcus* etc.

Lactic acid bacteria have been utilized as fermenting agents for the preservation of food taking benefit of a low pH and the action of fermentation products generated during the fermentative activity thereof to inhibit the growth of spoilage bacteria. In addition lactic acid bacteria have been used for preparing a variety of different foodstuff such as cheese, yogurt and other fermented dairy products from milk.

Quite recently lactic acid bacteria have attracted a great deal of attention in that some strains have been found to exhibit valuable properties to man and animals upon ingestion. In particular, specific strains of the genus *Lactobacillus* or *Bifidobacterium* have been found to be able to colonize the intestinal mucosa. Their temporary or sustained maintenance in the gut has been assumed to have numerous positive effects on the health of the beings having incorporating them.

In this respect, EP 0 768 375 discloses specific strains of the genus *Bifidobacterium*, that are capable to become implanted in the intestinal flora and may adhere to intestinal cells. These Bifidobacteria are reported to assist in immunomodulation, being capable to competitively exclude adhesion of pathogenic bacteria to intestinal cells, thus assisting in the maintenance of the individual's health.

During the last few years research has also focused on the potential use of lactic acid bacteria as probiotic agents. Probiotics are considered to be viable microbial preparations which promote the individual's health by preserving the natural microflora in the intestine. A microbial preparation may be commonly accepted as a probiotic in case the effectual microbes thereof and their mode of action are known. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

In this respect, WO 97/00078 discloses a specific strain, termed *Lactobacillus* GG (ATCC. 53103), as such a probiotic. The microorganism is particularly employed in a method of preventing or treating food induced hypersensitivity reactions in that it is administered to a recipient together with a food material that has been subjected to a hydrolysis treatment with pepsin and/or trypsin. The *Lactobacillus* strain selected is described as exhibiting adhesive and colonizing properties and showing a protease enzyme system, so that the protein material contained in the foodstuff to be administered is further hydrolyzed by means of proteases secreted by the specific *Lactobacillus* strain. The method discussed in this document shall eventually result in, the uptake of protein material by the gut that does not show a substantial amount of allergenic material anymore.

Further, in EP 0 577 903 reference is made to the use of such lactic acid bacteria having the ability of replacing *Heliobacter pylori*, the acknowledged cause for the development of ulcer, in the preparation of a support intended for the therapeutic or prophylactic treatment of an ulcer associated with the action of *Heliobacter pylori*.

In view of the valuable properties particular strains of lactic acid bacteria may provide, there is a desire in the art for additional lactic acid bacterial strains that are beneficial to the well being of man and/or animal.

A need, therefore, exists to provide additional bacterial strains that exhibit new properties beneficial for man and/or animals, such as pets.

SUMMARY

The present invention provides novel microorganisms belonging to the genus *Bifidobacterium* having the capability of preventing colonization of the intestine with pathogenic bacteria causing diarrhea and using them for the preparation of an ingestable support material.

The *Bifidobacterium* is selected from the group consisting of *Bifidobacterium longum* CNCM I-2169 and *Bifidobacterium longum* CNCM I-2170. *Bifidobacterium longum* (NCC 881) CNCM I-2169 and *Bifidobacterium longum* (NCC 490) CNCM I-2170 were deposited at the Collection Nationale de Cultures de Microorganismes Institut Pasteur at 25, Rue du Docteur Roux, F-75724 Paris Cedex 15, France on Mar. 15, 1999.

The microorganisms of the present invention have been shown to exhibit inter alia the following properties: they are gram positive, catalase negative and $CO_2$ production negative, they produce L(+) lactic acid and may essentially prevent colonization of intestinal cells by bacteria bringing about diarrhea, such as pathogenic *E. coli*, e.g. enteropathogenic *E. coli* (EPPC), or *salmonella*, e.g. *Salmonella typhimurium*.

In an embodiment, the novel microorganisms may be used for the preparation of a variety of ingestible support material, such as e.g. milk, yogurt, curd, fermented milks, milk based fermented products, fermented cereal based products, milk based powders, infant formula and pet food and may be included in the support in an amount of from about $10^5$ cfu/g to about $10^{11}$ cfu/g. For the purpose of the present invention the abbreviation cfu shall designate a "colony forming unit" that is defined as number of bacterial cells as revealed by microbiological counts on agar plates.

The present invention also provides a food or a pharmaceutical composition containing at least one of the above Bifidobacteria and/or containing a supernatant, in which the microorganisms have been grown or an active fraction thereof, respectively. In this respect it has been found that the supernatant of such bacteria also exhibits an anti-pathogenic activity.

For preparing a food composition according to the present invention at least one of the Bifidobacteria of the present invention is incorporated in a suitable support, in an amount of from about $10^5$ cfu/g to about $10^{12}$ cfu/g, preferably from about $10^6$ cfu/g to about $10^{10}$ cfu/g, more preferably from about $10^7$ cfu/g to about $10^9$ cfu/g.

In case of a pharmaceutical preparation the product may be prepared in form of tablets, liquid bacterial suspensions, dried oral supplements, wet oral supplements, dry tube feeding or a wet tube feeding with the amount of the *Bifidobacterium/Bifidobacteria* to be incorporated therein being in the range of up to about $10^{12}$ cfu/g, preferably from about $10^7$ cfu/g to about $10^{11}$ cfu/g, more preferably from about $10^7$ cfu/g to about $10^{10}$ cfu/g.

The activity of the novel microorganisms in the individual's intestine is of course dose dependent. That is, the more the novel microorganisms are incorporated by means of ingesting the above food material or the pharmaceutical composition the higher the protective and/or curing activity: of the microorganisms. Since the novel microorganisms are not detrimental to mankind and animals and have eventually, been isolated from baby feces a high amount thereof may be incorporated so that essentially a high proportion of the individual's intestine will be colonized by the novel microorganisms.

Yet, according to another embodiment the supernatant of a culture of a *Bifidobacterium* of the present invention, or an active fraction thereof, may be used for preparing the ingestable support. The supernatant may be used as such or may be dried under conditions that do not destroy the metabolic compounds secreted by the micro-organisms into the liquid medium, such as e.g. freeze drying, and may be included in the carrier. In order to minimize the number of unknown compounds in the supernatant the Bifidobacteria will preferably be grown in a defined media, the composition of which is known and does not negatively affect the host incorporating it. Further, the skilled person will, based on his general knowledge optionally deplete the supernatant from unwanted products, such as e.g. by means of chromatography.

Additional features and advantages of the present invention are described in, and will be apparent from, the following Detailed Description and the figures.

DETAILED DESCRIPTION

Figure 1:
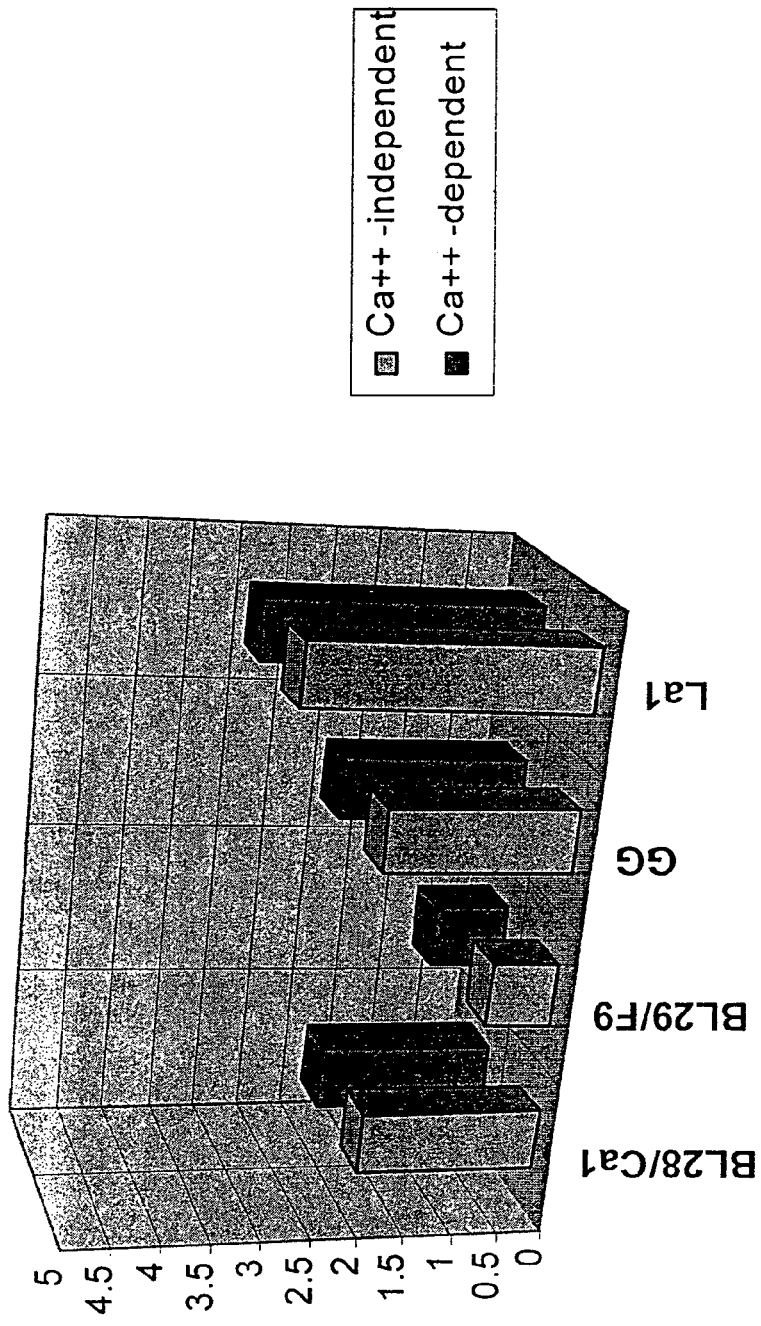
FIG. 1 shows a graph, indicating the capability of the cell lines CNCM I-2169 (termed B128/Ca1) and *Bifidobacterium longum* CNCM I-2170 (termed. BL29/F9) to adhere to human intestinal cells in culture.

During the extensive studies leading to the present invention the inventors have investigated baby feces and isolated a variety of different bacterial strains therefrom. These strains were subsequently examined for their capability to prevent colonization and/or invasion of epithelial cells with bacteria that are known to cause diarrhea, such as *E. coli, Sigella, Klebsiella, Yersinia, Pseudomnonas aeruginosa Listeria, Streptococcus, Staphilococcus, Clostridium difficile, H. pyori* and also *Candida albicans*.

Several bacterial genera comprising *Bifidobacterium, Lactococcus* and *Streptococcus* were screened for their diarrhea inhibitory properties. The tests for the inhibitory property were performed with pathogenic microorganisms, such as *E. coli, Klebsiella, Yersinia, Pseudomonas aeruginosa, H. pyori*, and *Salmonella typhimurium* as representatives for pathogenic microorganisms causing diarrhea in affected individuals.

The various bacteria were grown in a suitable medium, such as MRS, Hugo-Jago or M17 medium at temperatures of from about 30 to 40° C. corresponding to their optimal growth temperature. After reaching stationary growth the bacteria were collected by centrifugation and resuspended in physiological NaCl solution. Between the different tests the bacterial cells were stored frozen (–20° C.).

For assessing anti-bacterial properties the following approaches were chosen.

According to one protocol cultured Bifidobacteria of the present invention were examined for their capability to decrease the viability of the different pathogenic microorganisms. To this end, a culture of pathogenic bacteria was contacted with a concentrated supernatant of a *Bifidobacterium* culture and the growth potential of the pathogenic bacteria was assessed.

According to a second protocol the adhesion capability of the Bifidobacteria of the present invention to $T_{84}$ cells, a cell culture model for the intestine, was determined. To this end, the Bifidobacteria were cultured with $T_{84}$ cells and the rate of adhesion was assessed.

According to another protocol the potential of the Bifidobacteria of the present invention to prevent infection of intestinal cells by *Salmonella*, using the cell line Caco-2 as a model for the intestine, was determined. In this respect, the supernatant of a cell culture of the Bifidobacteria of the present invention was added together with the pathogenic microorganism to the intestinal cells and the rate of adhesion, or invasion, respectively, was assessed.

Thus, it could be shown that cultured Bifidobacteria and the supernatant proofed to be extremely effective in preventing both adhesion to and invasion into the intestinal cells indicating that metabolic compounds secreted by the novel microorganisms are likely to be responsible for the anti-diarrhea activity.

The present invention will now be described by way of examples without limiting the same thereto.

Media and Solutions:
MRS (Difco)
Hugo-Jago (tryptone 30 g/l (Difco), yeast extract 10 g/l (Difco), lactose 5 g/l (Difco), $KH_2PO_4$ 6 g/l, beef extract 2 g/l (Difco), agar 2 g/l (Difco))
M17 (Difco)
Eugon Tomato Agar (Canned tomato juice 400 ml, Eugon agar BBL 45.5 g, Maltose Difco 10 g, Hemin Sigma 5 mg, Agar Difco 5 g, distilled water 600 ml)
DMEM (Dulbecco's modified Eagle medium)
CFA (according to Ghosh et al. Journal of Clinical Microbiology, 1993 31 2163-6)
Müller Hinton agar (Oxoid)
LB (Luria Bertami, Maniatis, A Laboratory Handbook, Cold Spring Harbor, 1992)
$C^{14}$-acetate (53.4 Ci/nMol, Amersham International PLC)

PBS (NaCl 8 g/l, KCl 0.2 g/l, $Na_2HPO_4$ 1.15 g/l, $KH_2PO_4$ 0.2 g/l))
Trypsin-EDTA solution (Seromed)
FCS Fetal calf serum (Gibco)

*E. coli* DAEC C 1845 was obtained from Washington University, Seattle and *E. coli* JPN15 was obtained from the Center for Vaccine Development of the University of Maryland, USA).

The *Salmonella typhimurium* strain SL1344 was obtained from the department of Microbiology, Stanford University, CA, USA. This strain acts as a pathogen on mice and is resistant to Streptomycin. It adheres to Caco-2 colon cells (Finlay and Falkow, 1990).

The *Klebsiella* was obtained from stock clinical isolates from the microbiological laboratory of the Faculté de Pharmacie Paris XI, Châtenay-Malabry, France.

The *Yersinia* was obtained from INSERM Unit 411, Hôspital Necker, Paris, France.

The *Pseudomonas aeruginosa* was obtained from stock clinical isolates from the microbiological laboratory of the Faculté de Pharmacie Paris XI, Châtenay-Malabry, France.

The *H. pylori* was obtained from Institute of Microbiology, Lausanne University, Lausanne, Switzerland.

EXAMPLE 1

Isolation of Bifidobacteria

Fresh feces were harvested from diapers of 16 healthy babies 15 to 27 days old 1 g of fresh feces was placed under anaerobic conditions for transportation to the laboratory and microbiological analyses were run within 2 hours from sampling by serial dilutions in Ringer solution and plating on selective media. Eugon Tomato Agar (Canned tomato juice 400 ml, Eugon agar BBL 45.5 g, Maltose Difco 10 g, Hemin Sigma 5 mg, Agar Difco 5 g, distilled water 600 ml) incubated anaerobically at 37° C. for 48 hours was used to isolate bifidobacteria. Colonies were randomly picked up and purified. Physiological and genetic characterisation was performed on the isolates.

EXAMPLE 2

Cultivating Cell Lines

Caco-2 Cells:

For the inhibition assays the cell line Caco-2 was utilized as a model of mature enterocytes of the small intestine. This cell line presents characteristic of intestinal cells such as e.g. polarization, expression of intestinal enzymes, production of particular structural polypeptides etc. The cells were grown on different supports, namely on plastic dishes (25 $cm^2$, Corning) for growth and propagation, on defatted and sterilized 6 well glass plates (22×22 mm, Corning) for the adhesion and the inhibition tests. After the second day in culture the medium (DMEM) was changed on a daily basis. Before use the medium was supplemented with 100 U/ml penicilline/streptomycine, 1 µg/ml amphoterine, 20% FCS inactivated at 56° C. for 30 min and 1% of a solution containing non-essential amino acids (10 mM) (Eurobio, Paris, France). Culturing was performed at 37° C. in an atmosphere comprising 90% air and 10% $CO_2$. The cells were splitted every six days. The cells were detached from the walls of the well by treatment in PBS with 0.015% trypsine and 3 mM EDTA at pH 7.2. For neutralizing the effect of trypsine an equal volume of the culture medium containing FCS was added to the cell suspension obtained, the mixture was centrifuged. (10 min at 1000 rpm) and the pellet was again dissolved in culture medium. Living cells (not dyed with trypane blue) were counted. About $3.5\times10^5$ living cells were transferred to a new culture bottle and about $1.4\times10^5$ cells per well and cultivated until a confluent monolayer was obtained.

$T_{84}$ Cells:

For the adhesion assays the cell line $T_{84}$ was utilized as a model of colon cells from the intestine. This cell line presents characteristics of intestinal cells such as e.g. polarisation, expression of intestinal enzymes, production of particular structural polypeptides etc. $T_{84}$ cells were obtained from University of California, San Diego, Calif. Cells were grown in DMEM (50%) and Ham's F12 (50%) supplemented with 2 mM glutamine, 50 mM HEPES, 1% non-essential amino acids and 10% inactivated (30 min, 56° C.) fetal calf serum (Boehringer, Mannheim, Germany) at 37° C. in a 10% $CO_2$/90% air atmosphere. Cells were seeded at a concentration of $10^6$ cells per $cm^2$. Cells were used for adherence assays at late post-confluence, i.e., after 10 days.

All strains except Bifidobacteria were kept at −80° C. in their culture medium containing 15% glycerol. As the number of transfers into new media has an influence on the adhesion factors, the *Salmonella* strain was only transferred twice within a period of 24 hours, the first transfer taking place when the strain was frozen. All cultures were raised aerobically.

Bifidobacteria

The bacterial strains (*Bifidobacterium longum* CNCM I-2169 (B129/Ca1) and *Bifidobacterium longum* CNCM I-2170 (BL29/F9)) were stored at −20° C. in MRS medium containing 15% glycerol. The strains were grown under anaerobic conditions in MRS and transferred twice to new media at intervals of 24 hours before use in the inhibition assays. For the assay a concentration of $2\times10^9$ cfu/ml was utilized. The supernatant was collected by centrifugation for 1 hour at 20.000 rpm and the supernatant obtained was subsequently checked for the presence of bacteria. The strains of *Bifidobacterium* were cultivated anaerobically in MRS during 18 hours at 37° C. The cultures were then centrifuged (20 min. at 4° C.), the supernatant was collected, lyophilized, returned to the solution and then concentrated ten times (10×). The pH of the supernatant was finally adjusted to 4.5.

*E. coli* C 1845:

The first passage after thawing was effected on a CFA—Müller Hinton agar, which is suitable to effect expression of adhesion factors by the bacterium. Before each experiment the bacterial cells were incubated at 37° C. with a transfer to a new medium being effected twice after 24 hours each.

*Klebsiella*:

Bacteria were grown overnight for 18 hrs at 37° C. in Luria broth.

*Yersinia*:

Bacteria were grown overnight for 18 hrs at 37° C. in Luria broth.

*Pseudomonas aerupinosa*:

Bacteria were grown overnight for 18 hrs at 37° C. in Luria broth.

*H. pylori*:

Bacteria were grown on Brain-Heart Infusion (BHI)-agar plates containing 0.25% yeast extract (Difco Laboratories, Detroit, Mich.), 10% horse serum and 0.4% Campylobacter selective complement (Skirrow supplement, SR 69; Oxoid Ltd, Basingstoke, England).

EXAMPLE 4

Adhesion of B128/Ca1 and BL29/F9 to $T_{84}$ and Caco-2Cells

The Caco-2 and $T_{84}$ monolayers, prepared on glass coverslips which were placed in six-well Corning tissue culture plates (Corning Glass Works, Corning, N.Y.), were washed twice with phosphate-buffered saline (PBS). Bifidobacteria (1 ml, $4 \times 10^8$ bacteria/ml in spent culture supernatant, treated-supernatant or fresh MRS broth) were added to 1 ml of the cell line culture medium. This suspension (2 ml) was added to each well of the tissue culture plate and the plate incubated at 37° C. in 10% $CO_2$/90% air. After 1 hour of incubation, the monolayers were washed five times with sterile PBS, fixed with methanol, stained with Gram stain, and examined microscopically. Each adherence assay was conducted in duplicate over three successive passages of intestinal cells. For each monolayer on a glass coverslip, the number of adherent bacteria was evaluated in 20 random microscopic areas. Adhesion was evaluated by two different technicians to eliminate bias.

The results are shown in FIG. 1 from which it becomes obvious that both of B128/Ca1 and BL29/F9 are capable to adhere to intestinal cells comparable to the known cell line GG (WO 97/00078) or La1 (EP 0 577 903).

EXAMPLE 5

Anti-Pathogenic Activity of the Bifidobacteria

As candidates for pathogenic bacteria *E. coli*, *Klebsiella*, *Yersinia*, *Pseudomonas aeruginosa* and *H. pyori* were used.

Based on a culture of bacteria (B128/Ca1 or BL29/F9) kept in MRS medium for 18 hours, an exponentially growing culture was produced (3 hours at 37° C.). 2 ml of this solution were removed and centrifuged for 5 min. at 5500 g, +4° C. After collection of the supernatant the cell pellet was washed in sterile PBS. After centrifuging, the pellet was collected and 2 ml of sterile PBS were added. The bacteria were counted and the suspension was adapted in such a way that between 1 and $5 \times 10^6$ bacteria/ml were produced.

Figure 2:
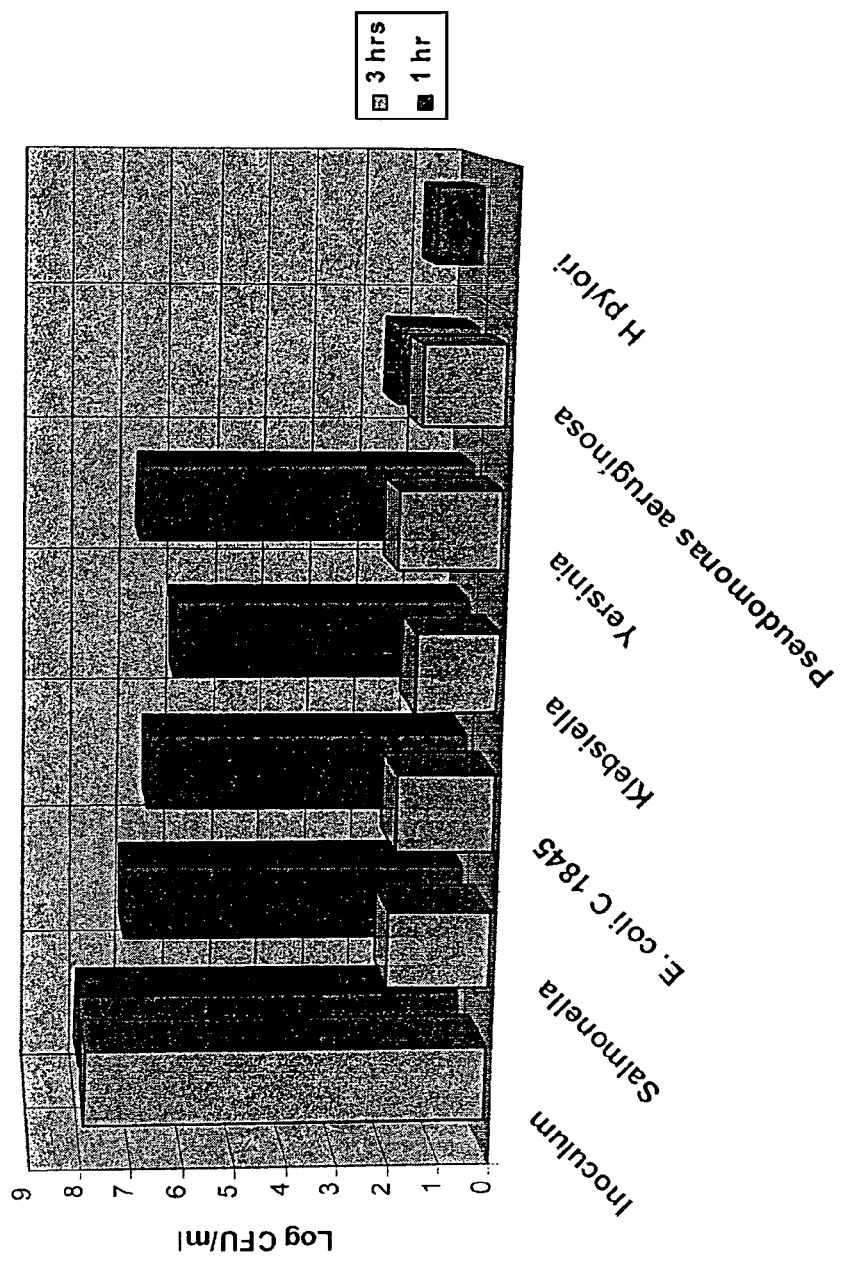
FIG. 2 shows the pathogen sensitivity of pathogenic bacteria towards *Bifidobacterium longum* CNCM I-2170 (BL29/F9).
Figure 3:
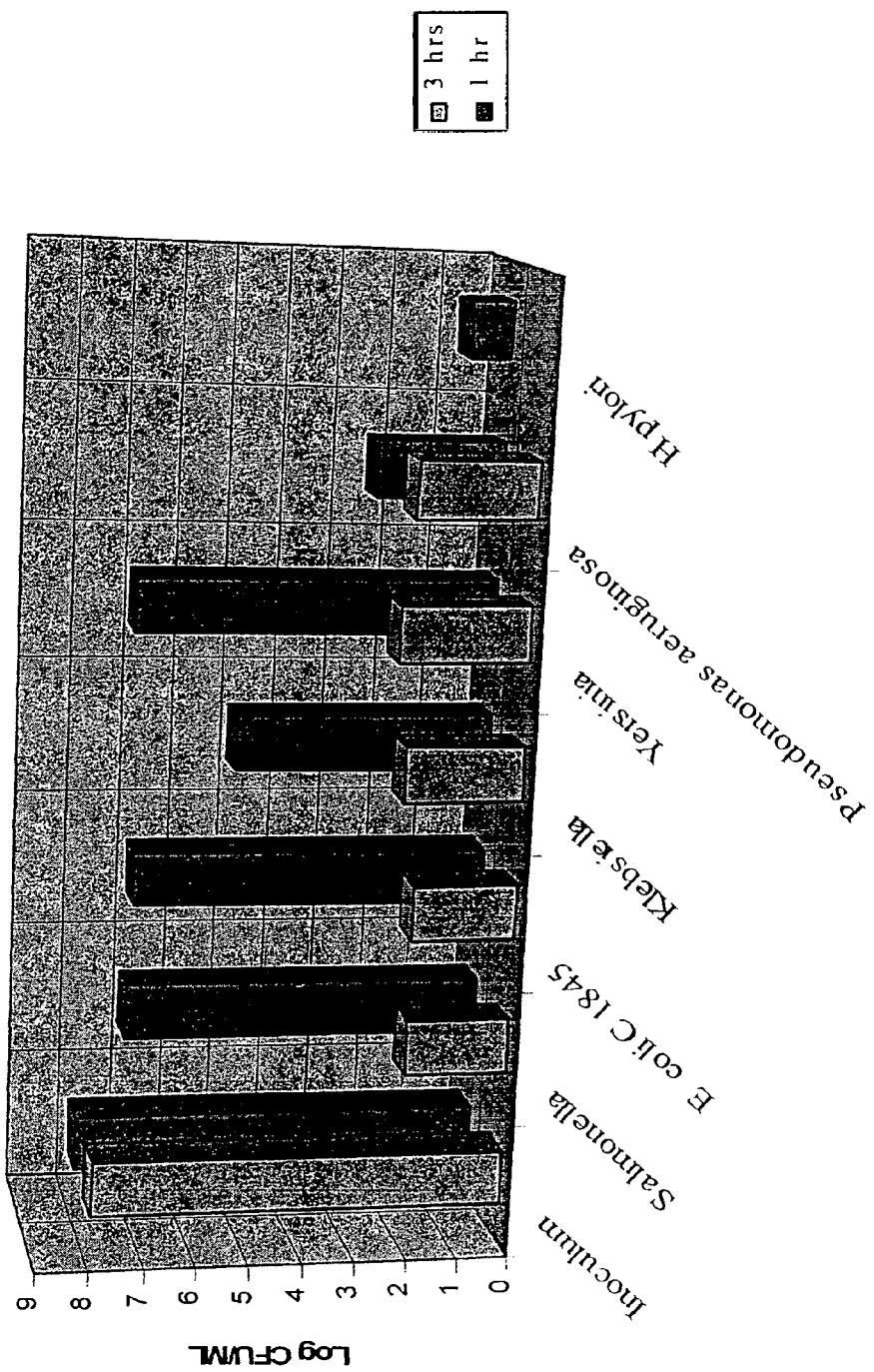
FIG. 3 shows the pathogen sensitivity of pathogenic bacteria towards *Bifidobacterium longum* CNCM I-2169 (B128/Ca1).
Figure 4:
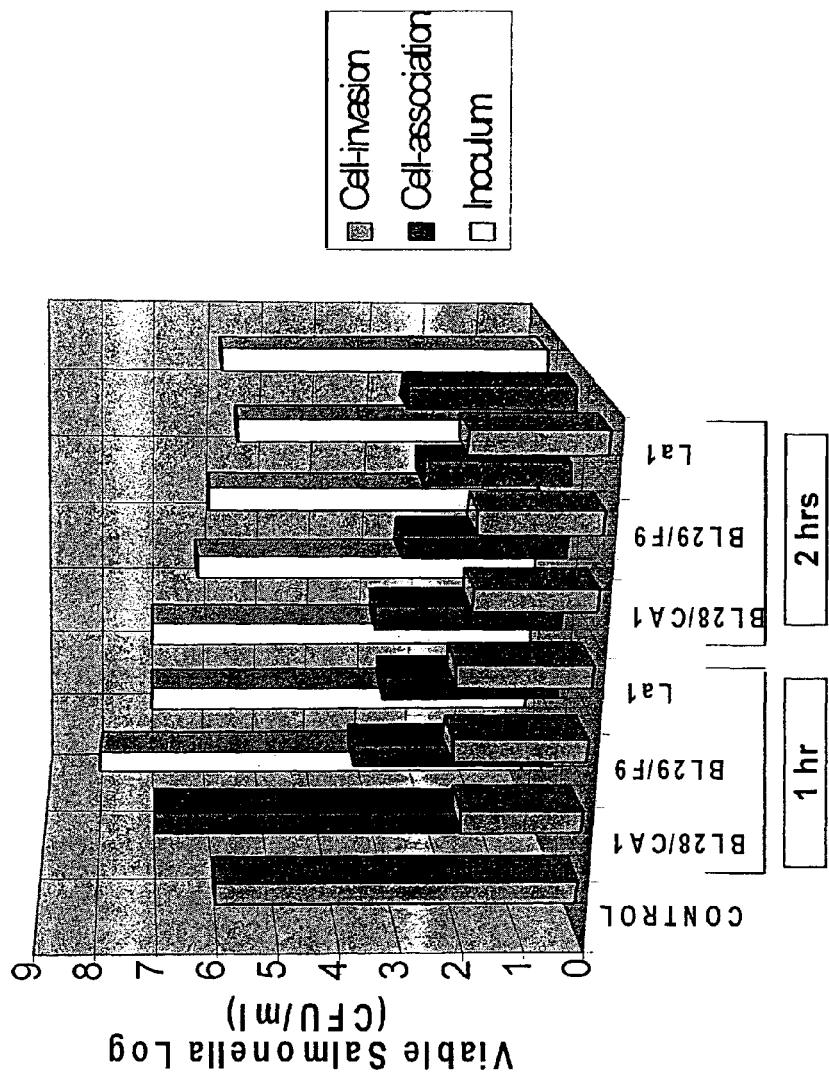
FIG. 4 shows the activity of the cell lines B128/Ca1 and BL29/F9 against *S. typhimurium* SL1344 infecting Caco-2 cells.

The assessment of the antimicrobial effect exerted by the Bifidobacteria of the present invention was carried out according to the Lehrer method described in Lehrer et al., J. Imunol. Methods 137 (1991), 167-173, which document is incorporated here by way of reference. The results thereof are shown in FIGS. 2 and 3.

From the above results it may be seen that the Bifidobacteria of the present invention may effectively inhibit growth of the various pathogenic bacteria.

EXAMPLE 6

Inhibition Assay for *salmonella*

*Salmonella* are bacteria that invade epithelial cells and multiply therein. For determining the inhibitory activity of the Bifidobacteria of the present invention towards *Salmonella typhimurium* the strain SL 1344 and following procedure was used.

The pathogenic cells were cultivated in LB-medium. After the second passage to new medium the bacterial strains were marked with radioisotopes using $C^{14}$-acetate at 10 µCi/ml in LB-medium. Incubation of the strains in this medium was performed for 18 hours at 37° C.

The bacterial suspension was subsequently subjected to centrifugation (1041 rpm, 15 min) so as to eliminate the remaining $C^{14}$-acetate from the supernatant. The pellet was suspended and washed in PBS and the cells were suspended at a concentration of about $10^8$ cells/ml in 1% sterile mannose. Mannose is known to inhibit non specific adhesion. The bacterial solution was then adjusted to $2 \times 10^8$ cells/ml.

The pathogen (1 ml; $2 \times 10^8$ cells) and an aliquot of a supernatant (1 ml) of a *Bifidobacterium* culture are pre-incubated for 2 hours at 37° C. The suspension is subsequently centrifuged, the resulting supernatant is removed and the pellet is again suspended in 0.5 ml PBS. This pathogen solution (0.5 ml) is then brought in contact with human intestine cells in culture.

The culture was washed with sterile PBS twice and 0.5 ml adhesion medium (DMEM) was added. The cells are then incubated for 1 hour at 37° C. under 10% $CO_2$.

After incubation the number of bacteria in the incubation medium and on/in the intestinal cells are counted. In order to determine the amount of cells adhering on or having invaded into the intestinal cells the following approaches have been chosen.

For determining the number of adhering bacteria the medium was decanted and the cells were washed once with culture medium and once with sterile PBS. Subsequently, 1 ml of sterile $H_2O$ was added per compartment, to lyse the cells and to form a cell solution which was incubated for 1-2 hours at 37° C., after which successive dilutions were carried out. In order to count the number of adhering and invasive-bacteria, the cell solution was centrifuged to remove cell debris and the radioactivity was measured.

According to another protocol 10 aliquots were each put on TSA medium. The media were then incubated for 18-24 hours at 37° C.

For determining the amount of invaded bacteria the Caco-2 cells were washed with PBS so as to eliminate all non-adhering cells. Subsequently, a medium containing gentamycin (20 µg/ml) was added and incubation was continued for 1 hour at 37° C. Gentamycin is an antibiotic not penetrating intestinal cells so that all extracellular microorganisms were killed, while bacteria having already invaded intestinal cells will survive. The cells were then incubated for another hour at 37° C. and were then washed twice with PBS. The cells were lysed by addition of and incubation in sterile distilled water for 1-2 hours at 37° C. After removing the cell debris radioactivity was determined. According to another protocol successive dilutions were carried out, which were put on TSA medium. Incubation: 18-24 hours at 37° C.

It may be seen that cultured cells and the culture supernatant were extremely effective in preventing adhesion of and invasion into intestinal cells by *Salmonella*.

EXAMPLE 7

Infection of Mice by the Strain *S. typhimurium* C5

Adult, 7-8 weeks old, axenic, female mice (C3H/He/oujco conventional, Iffa Credo, France), raised under sterile conditions, were orally infected with a fixed concentration of *S. typhimurium* (0.2 ml, $10^8$ cfu/mouse). Some mice were rendered monoxenic by the implantation of a range of Bifidobacteria strains. With some mice, the Bifidobacteria in segments of the intestine were counted after its removal and mincing of the organs in PBS. With other mice, the protection against infection was assessed in such a way that they were continuously kept in a sterile environment and the days of survival were compared to the control group.

Figure 5:
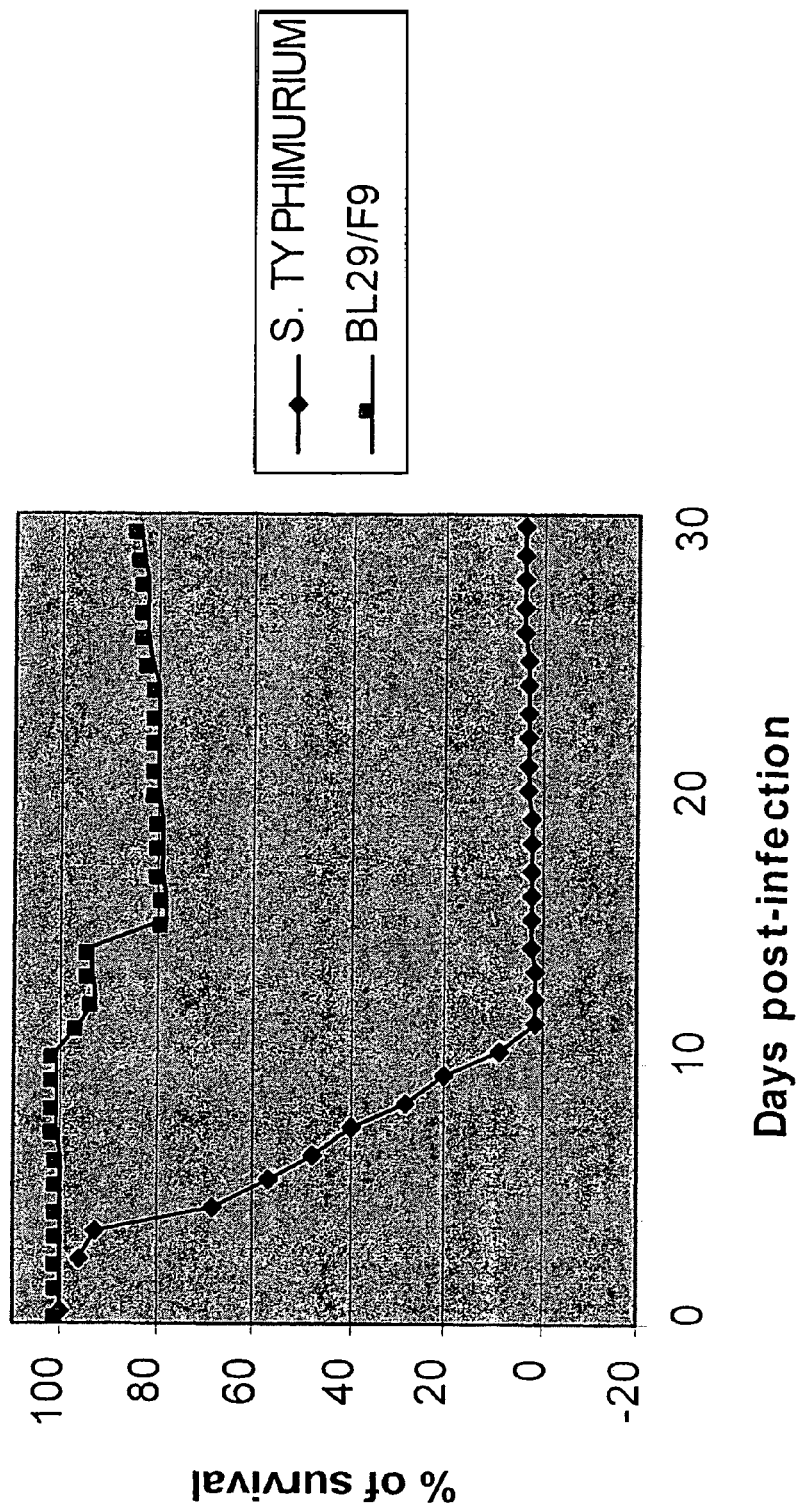
FIG. 5 shows the rate of survival of mice infected with *Salmonella typhimurium* SL 1344 and treated with the *Bifidobacterium* BL29/F9.

The results are shown in FIG. 5. As may be derived therefrom in the control group nearly all mice died after a time period of about 10 days. In contrast thereto, all mice treated with BL29/F9 were alive after 10 days with only 20% dying from the detrimental effect exerted by *Salmonella* after a period of 30 days.

These results show the extreme superior properties of the Bifidobacteria of the present invention.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An ingestible composition capable of preventing colonization of bacteria causing diarrhea comprising a biologically pure culture of *Bifidobacterium* selected from the group consisting of *Bifidobacterium longum* CNCM I-2169 and *Bifidobacterium longum* CNCM I-2170, wherein the composition is a food composition comprising about $10^5$ cfu/g to about $10^{12}$ cfu/g of the *Bifidobacterium* culture.

2. An ingestible composition capable of preventing colonization of bacteria causing diarrhea comprising a biologically pure culture of *Bifidobacterium* selected from the group consisting of *Bifidobacterium longum* CNCM I-2169 and *Bifidobacterium longum* CNCM I-2170, wherein the composition is a pharmaceutical composition comprising about $10^7$ cfu/g to about $10^{12}$ cfu/g of the *Bifidobacterium* culture.

3. An ingestible composition capable of preventing colonization of bacteria causing diarrhea comprising a biologically pure culture of *Bifidobacterium* selected from the group consisting of *Bifidobacterium longum* CNCM I-2169 and *Bifidobacterium longum* CNCM I-2170, wherein the *Bifidobacterium* culture ranges in concentration from about $1 \times 10^6$ cells/ml to about $5 \times 10^6$ cells/ml.

* * * * *